US008333994B2

(12) United States Patent
Katti et al.

(10) Patent No.: US 8,333,994 B2
(45) Date of Patent: Dec. 18, 2012

(54) STABILIZED, BIOCOMPATIBLE GOLD NANOPARTICLES AND ENVIRO-FRIENDLY METHOD FOR MAKING SAME

(75) Inventors: Kattesh V. Katti, Columbia, MO (US); Raghuraman Kannan, Columbia, MO (US); Kavita K. Katti, Columbia, MO (US); Satish Kumar Nune, Lawrence, KS (US)

(73) Assignee: The Curators of the University of Missouri, Columbia, MO (US)

( * ) Notice: Subject to any disclaimer, the term of this patent is extended or adjusted under 35 U.S.C. 154(b) by 863 days.

(21) Appl. No.: 12/283,935

(22) Filed: Sep. 17, 2008

(65) Prior Publication Data

US 2009/0074674 A1 Mar. 19, 2009

Related U.S. Application Data

(60) Provisional application No. 60/994,111, filed on Sep. 17, 2007.

(51) Int. Cl.
*A61K 9/14* (2006.01)
(52) U.S. Cl. ..................................... 424/489
(58) Field of Classification Search .................. None
See application file for complete search history.

(56) References Cited

U.S. PATENT DOCUMENTS

| 5,541,289 | A | 7/1996 | Gilbertson |
| 6,103,868 | A | 8/2000 | Heath et al. |
| 6,572,673 | B2 | 6/2003 | Lee et al. |
| 6,818,199 | B1 | 11/2004 | Hainfeld et al. |
| 2005/0009170 | A1* | 1/2005 | Gardea-Torresdey et al. ................. 435/262 |
| 2005/0054613 | A1 | 3/2005 | Katti et al. |
| 2006/0127505 | A1* | 6/2006 | Haines et al. ................. 424/729 |
| 2007/0051202 | A1* | 3/2007 | Raghuraman et al. .......... 75/370 |
| 2007/0299133 | A1* | 12/2007 | Mehansho et al. ............. 514/547 |
| 2008/0076119 | A9* | 3/2008 | Sun et al. ........................... 435/6 |
| 2009/0232853 | A1* | 9/2009 | Harris ........................... 424/400 |

FOREIGN PATENT DOCUMENTS

| WO | WO 03/072053 | 9/2003 |
| WO | WO 2007/027978 | 3/2007 |
| WO | WO 2009/005752 | 1/2009 |

OTHER PUBLICATIONS

Balogh, Lajos P. Shraddha S. Nigavekar, Andrew C. Cook, Leah Minc, Khan, Mohamed K., "Development of dendrimer-gold radioactive nanocomposites to treat cancer microvasculature," *Biotechnology*, vol. 2, No. 4, 2003, pp. 94-44.
Santanu Bhattacharya et al. "Synthesis of gold nanoparticles stabilised by metal-chelator and the controlled formation of close-packed aggregates by them," Proc. Indian Acad. Sci. (Chem. Sci), vol. 115, Nos. 5 & 6, Oct.-Dec. 2003, pp. 613-619.
Brust M., Walker M., Bethell D., Schiffrin D.J., Whyman R., "Synthesis of Thiol-Derivatised Gold Nanoparticles in a Two-Phase Liquid-Liquid System", *Journal of the Chemical Society-Chemical Communications*, vol. 7, 1994, pp. 801-802.
Chen J., Saeki F., Wiley B.J., Cang H., Cobb M.J,. Li Z-Y, et al. "Gold Nanocages: Bioconjugation and Their Potential Use as Optical Imaging Contrast Agents", *Nano Letters*, vol. 5, No. 3, 2005; pp. 473-477.
Jorge Gardea-Torresdey, "Plants with Midas Touch: Formation of Gold Nanoparticles by Alfalfa Plants," Believed published circa 2002 on the World Wide Web at: http://www-ssrl.slac.stanford.edu/research/highlights_archive/alfalfa.html.
Gierada, D. S.; Bae, K. T., "Gadolinium as a CT contrast agent: Assessment in a porcine model", *Radiology*, vol. 210, 1999, pp. 829-834.
Hainfeld, J. F.; Slatkin, D. N.; Focella, T. M.; Smilowitz, H. M., "Gold nanoparticles: a new X-ray contrast agent", *British Journal of Radiology*, vol. 79, 2006, pp. 248-253.
S. He et al., "Superlattices of Silver Nanoparticles Passivated by Mercaptan," *Journal of Physics D: Applied Physics*, vol. 34, 2001, pp. 3425-3429.
L. Kalaugher, "Green Technique Makes Silver Nanoparticles,", www.nanotechweb.org/articles/news/3/1/1/1, Jan. 2004.
Kannan R, Rahing V, Cutler C, Pandrapragada R, Katti KK, Kattumuri V, et al., "Nanocompatible chemistry toward fabrication of target-specific gold nanoparticles", *Journal of the American Chemical Society*, vol. 128, No. 35, 2006; pp. 11342-11343.
Kattumuri, V.; Katti, K.; Bhaskaran, S.; Boote, E. J.; Casteel, S. W. et al., "Gum arabic as a phytochemical construct for the stabilization of gold nanoparticles: In vivo pharmacokinetics and X-ray-contrast-imaging studies", *Small*, vol. 3, No. 2, 2007, pp. 333-341.
Kattumuri V, Chandrasekhar M, Guha S, Raghuraman K, Katti K.V, Ghosh K, et al., "Agarose-stabilized gold nanoparticles for surface-enhanced Raman spectroscopic detection of DNA nucleosides", *Applied Physics Letters*, vol. 88, No. 15, 2006, pp. 153114-1-153114-3.
Beomseok Kim et al., "Tuning the Optical Properties of Large Gold Nanoparticle Arrays," *Mat. Res. Soc. Symp. Proc.*, vol. 676, 2001.
Beomseok Kim et al., "Self-Organization of Large Gold Nanoparticle Arrays," *J. Am. Chem. Soc.*, vol. 123, 2001, pp. 7955-7956.

(Continued)

*Primary Examiner* — Susan Tran
(74) *Attorney, Agent, or Firm* — Greer, Burns & Crain Ltd.

(57) ABSTRACT

The invention provides stabilized, biocompatible gold nanoparticles that are stabilized with material from polyphenols- or flavanoids-rich plant material or reactive phytochemical components of the plant material. The gold nanoparticles of the invention can be fabricated with an environmentally friendly method for making biocompatible stabilized gold nanoparticles. In methods of the invention, an aqueous solution containing gold salts is mixed with polyphenols- or flavanoids-rich plant material. In preferred embodiment methods of making, an aqueous solution containing gold salts is provided. The aqueous solution is mixed with black tea, turmeric, curcumin or cinnamon or a similar naturally occurring polyphenols- or flavanoids-rich plant material. The gold salts react to form biocompatible gold nanoparticles that are stabilized with a coating of the polyphenols- or flavanoids-rich plant material. The black tea, turmeric, curcumin or cinnamon or similar naturally occurring polyphenols- or flavanoids-rich plant material can be a powder or can be in its root or bark form.

18 Claims, 5 Drawing Sheets

OTHER PUBLICATIONS

I. Pastoriza-Santos et al.. "Reduction of Silver Nanoparticles in DMF. Formation of Monolayers and Stable Colloids,", *Pure Appl. Chem.*, vol. 72, Nos. 1-2, 2002, pp. 83-90.

Peters R., "Nanoscopic medicine: The next frontier", *Small* vol. 2, No. 4, 2006 pp. 452-456.

Kandikere Ramaiah Prabhu et al. "*De novo* synthetic design for air-stable *bis* primary phosphines: Synthetic, catalytic and biomedical motifs," Special Section: Non-Metal Chemistry; Current Science, vol. 78, No. 4, Feb. 25, 2000.

Rosset, A.; Spadola, L.; Ratib, O., "OsiriX: An open-source software for navigating in multidimensional DICOM images", *Journal of Digital Imaging*, vol. 17. No. 3, 2004, pp. 205-216.

Sokolov K, Aaron J, Hsu B, Nida D, Gillenwater A, Follen M, et al., "Optical systems for In vivo molecular imaging of cancer", *Technology in Cancer Research & Treatment*, vol. 2, No. 5, 2003, pp. 487-594.

Spring, D. B.; Barkan, H. E.; Bettmann, M. A., Dr Spring and colleagues respond: Safety of ionic and nonionic contrast media, *Radiology*, vol. 206, 1998, pp. 560-561.

Spring, D. B.; Bettmann, M. A.; Barkan, H. E., "Nonfatal adverse reactions to iodinated contrast media: Spontaneous reporting to the U.S. Food and Drug Administration, 1978-1994", *Radiology*, vol. 204, 1997, pp. 325-332.

Spring, D. B.; Bettmann, M. A.; Barkan, H. E., "Deaths related to iodinated contrast media reported spontaneously to the U.S. Food and Drug Administration, 1978-1994: Effect of the availability of low-osmolality contrast medial", *Radiology*, vol. 204, 1997, pp. 333-337.

Wagner V, Dullaart A, Bock AK, Zweck A., "The emerging nanomedicine landscape", *Nature Biotechnology*, vol. 24, No. 10, 2006; pp. 1211-1217.

Yin et al., "Synthesis and Characterization of Stable Aqueous Dispersion of Silver Nanoparticles Through the Tollens Process," *J. Mater. Chem.*, vol. 12, 2002, pp. 522-527.

* cited by examiner

US 8,333,994 B2

STABILIZED, BIOCOMPATIBLE GOLD NANOPARTICLES AND ENVIRO-FRIENDLY METHOD FOR MAKING SAME

PRIORITY CLAIM AND REFERENCE TO RELATED APPLICATION

The application claims priority under 35 U.S.C. §119 from prior provisional application Ser. No. 60/994,111, which was filed on Sep. 17, 2007.

STATEMENT OF GOVERNMENT INTEREST

This invention was made with government support under contract no. R01CA119412 awarded by the National Cancer Institute. The government has certain rights in the invention.

FIELD

A field of the invention is gold nanoparticles. Example applications of the invention include medical diagnostics and medical therapies. Non-medical applications include sensors and electronic materials. Gold nanoparticles find use as therapeutic agents, sensors, electronic materials and coatings on biological and non-biological surfaces.

BACKGROUND

Nanomedicine is an emerging area of medicine that utilizes nanoparticles for the detection and treatment of various diseases and disorders. Nanoparticles are tiny fragments of metals (or non metals) that are 100,000 times smaller than the width of human hair. Nanoparticles typically have different properties than naturally occurring bulk materials. Collateral properties emanate when materials, especially metals, are reduced to dimensions measured in nanometers. Nanoparticles exhibit properties that are unique from their corresponding naturally occurring bulk material.

Nanoparticles within the size range of about 1-50 nanometers have a size that can be correlated to cells, viruses, proteins and antibodies. The size resemblance that such nanoparticles have to living cells and cell components are of great interest to medical research because cells are primary components of all life (humans and animals).

Gold nanoparticles have a number of important potential medical applications. One application is hyperthermia treatment in which gold nanoparticles are heated with oscillating magnetic fields after being associated with a targeted cell, typically cancer cells. Other applications relate to biological imaging, as gold nanoparticles display photo absorbance or emission characteristics that can be used in imaging for the diagnosis of various diseases. Contrast enhancement is also provided by gold nanoparticles. For example, the selective absorption of X-rays by gold and other metallic nanoparticles provides measurable contrasts for use in computer tomographic (CT) imaging and other imaging techniques These and other important diagnostic and therapeutic properties are attainable only when metallic (or non metallic) materials are reduced to nanometer particle sizes.

Gold nanoparticles have unique properties that make them more attractive than other nanoparticles for many therapeutic, imaging, and sensing applications, and particularly in medical applications. Gold nanoparticles have an unoxidized state, whereas most of the surface of less noble metals get oxidized to a depth of several nanometers or more, often significantly reducing or obliterating the nanoscale properties of the nanoparticles. Gold nanoparticles are highly reactive, but biocompatible, making them especially well-suited for in vivo imaging and therapy. Gold nanoparticles can also be coated with specific biomolecules including, monoclonal antibodies, aptamers, peptides and various receptor specific substrates. Receptor specific coated nanoparticles are used mainly for targeting three different markers that are over expressed on cancer cells. They include: matrix metalloproteases, epidermal growth factor receptor, and oncoproteins that are associated with human papillomavirus infection.

For such in vivo imaging and therapy applications, it is that gold nanoparticles be produced stabilized in a biologically benign medium. Many current methods of producing gold nanoparticles require the removal of unreacted chemicals and byproducts from the nanoparticles as the chemicals and byproducts are necessary to the synthesis of the gold nanoparticles. The chemicals and byproducts must be removed after the production of nanoparticles to make the nanoparticles biocompatible.

Typical known methods of making nanoparticles utilize harsh conditions, such as the application of sodium borohydride to reduce $AuCl_4^-$. See, e.g., M. Brust et al, "Synthesis of Thiol-Derivatized Gold Nanoparticles in a 2-Phase Liquid-Liquid System" Journal of the Chemical Society-Chemical Communications (7):801-02 (1994). The method provides for the efficient production of gold nanoparticle, but is unsuitable in the presence of target specific peptides because sodium borohydride will reduce chemical functionalities present on peptide backbones, which can reduce or eliminate the biospecificity of biomolecules. The sodium borohydride reduction method also uses thiols to stabilize the gold nanoparticles from agglomeration. Thiol-gold nanoparticle interaction is strong and makes gold nanoparticles highly stable. Once the gold nanoparticles are stabilized by thiols, they cannot be readily transferred onto useful drug moieties including peptides, proteins and various biochemical vectors that are normally used to target diagnostic and therapeutic gold nanoparticles on to tumor and various disease sites in the body. Other methods that have been developed utilize chemical cocktails during nanoparticle production, and are not environmentally friendly in additional to having the drawbacks concerning stabilization, reactivity, and biocompatibility.

SUMMARY OF THE INVENTION

The invention provides stabilized, biocompatible gold nanoparticles that are stabilized with material from polyphenols- or flavanoids-rich plant material or reactive phytochemical components of the plant material. The gold nanoparticles of the invention can be fabricated with an environmentally friendly method for making biocompatible stabilized gold nanoparticles. In methods of the invention, an aqueous solution containing gold salt is mixed with polyphenols- or flavanoids-rich plant material. In preferred embodiment methods of making, an aqueous solution containing gold salts is provided. The aqueous solution is mixed with black tea, turmeric, curcumin or cinnamon or a similar naturally occurring polyphenols- or flavanoids-rich plant material. The gold salts react to form biocompatible gold nanoparticles that are stabilized with a coating of the polyphenols- or flavanoids-rich plant material. The black tea, turmeric, curcumin or cinnamon or similar naturally occurring polyphenols- or flavanoids-rich plant material can be a powder or can be in its root or bark form.

DETAILED DESCRIPTION OF THE PREFERRED EMBODIMENTS

Figure 1:
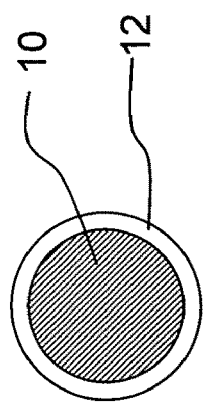
FIG. 1 is a schematic diagram that illustrates a stabilized, biocompatible gold nanoparticle of the invention.

The invention provides stabilized, biocompatible gold nanoparticles that are stabilized with material from polyphenols- or flavanoids-rich plant material. The gold nanoparticles of the invention can be fabricated with an environmentally friendly method for making biocompatible stabilized gold nanoparticles. In methods of the invention, an aqueous solution containing gold salts is mixed with polyphenols- or flavanoids-rich plant material.

In preferred embodiment methods of making, an aqueous solution containing gold salts is provided. The aqueous solution is mixed with black tea, turmeric, curcumin or cinnamon or a similar naturally occurring polyphenols- or flavanoids-rich plant material. The gold salts react to form biocompatible gold nanoparticles that are stabilized with a coating of the polyphenols- or flavanoids-rich plant material. The black tea, turmeric, curcumin or cinnamon or similar naturally occurring polyphenols- or flavanoids-rich plant material can be a powder or can be in its root or bark form.

Stabilized, biocompatible gold nanoparticles of the invention demonstrate an affinity for cancer cells and tissues. Accordingly, stabilized, biocompatible gold nanoparticles of the invention are well suited for diagnostic and therapeutic techniques that rely upon gold nanoparticles for imaging, contrast, or cell destruction. A method of sensing or therapy of the invention comprises introducing stabilized, biocompatible gold nanoparticles of the invention into a human or animal subject and conducting gold nanoparticle enhanced imaging or gold nanoparticle enhanced therapy.

Fabrication methods of the invention require only gold salts as precursors. No other man-made chemicals are employed in the overall fabrication process, and there are accordingly no harsh chemicals utilized in the fabrication or harsh byproducts formed during the fabrication. Fabrication processes of the invention are therefore environmentally friendly and biologically benign.

Gold nanoparticles produced by methods of the invention demonstrate a high affinity for cancer cells/tissue. Embodiments of the invention include the diagnostic and therapeutic use of gold nanoparticles produced by methods of the invention in molecular imaging and therapy of cancer and various diseases in animals and human subjects.

Preferred embodiment gold nanoparticles of the invention are gold nanoparticles that are stabilized with ingredients from black tea, turmeric, curcumin or cinnamon or similar naturally occurring materials or specific components of the materials. Similar naturally occurring materials include spices and herbs that are related to the botanical family of tea, turmeric and cinnamon. Similar materials further include other polyphenols- or flavanoids-rich plant based materials.

Example preferred embodiments for making gold nanoparticles include steps of reacting a gold salt with polyphenols- or flavanoids-rich plant based materials to produce biocompatible gold nanoparticles. Exemplary polyphenols- or flavanoid-rich plant materials include tea, cinnamon, turmeric or curcumin. In exemplary methods of the invention, very high conversion is achieved in relatively short times and at room temperature. Embodiments of the invention include biocompatible gold nanoparticles produced through this environmentally friendly process.

Preferred embodiments will now be discussed with respect to the drawings. The description includes descriptions of experiments. The drawings include schematic figures that are not to scale, which will be fully understood by skilled artisans with reference to the accompanying description. Features may be exaggerated for purposes of illustration. From the preferred embodiments and experiments, artisans will recognize additional features and broader aspects of the invention.

FIG. 1 is a schematic diagram that illustrates a stabilized, biocompatible gold nanoparticle of the invention. In FIG. 1, a gold nanoparticle 10 is coated with a layer of polyphenols- or flavanoids-rich plant material 12.

Figure 2:
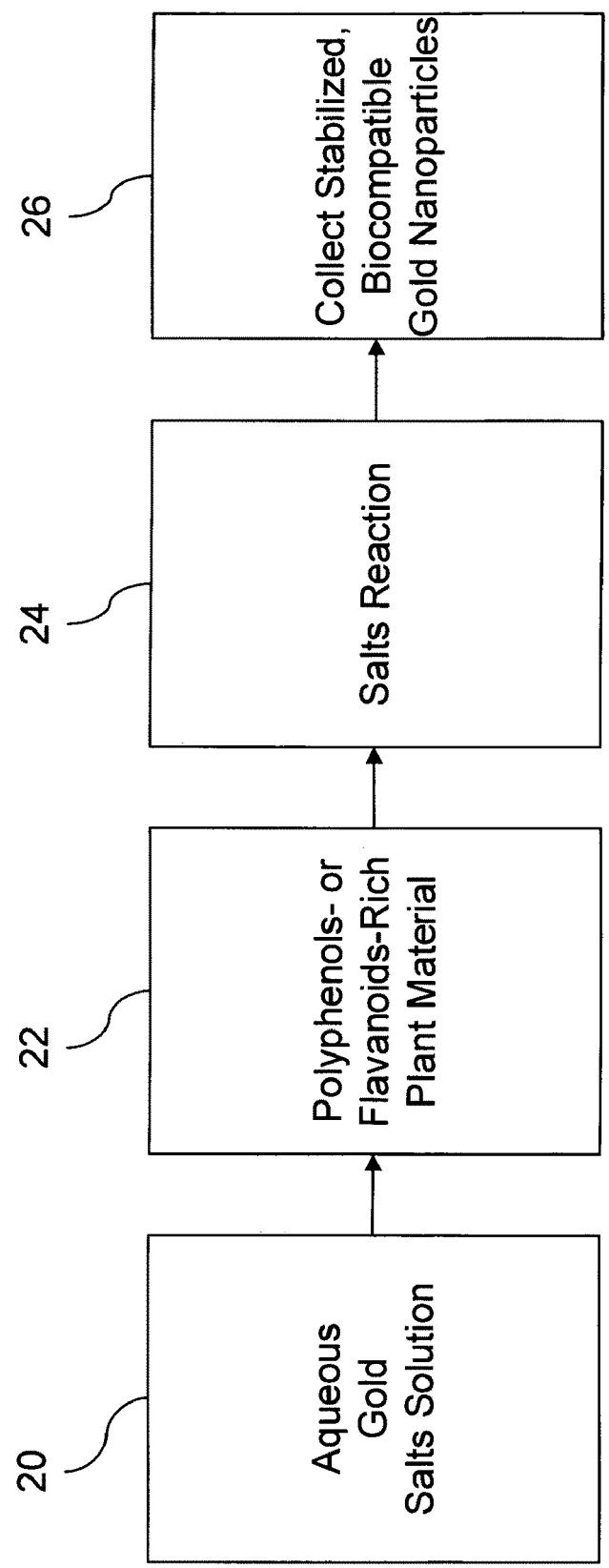
FIG. 2 illustrates a preferred method of fabricating a stabilized, biocompatible gold nanoparticle of the invention.

FIG. 2 illustrates a preferred method of fabricating a stabilized, biocompatible gold nanoparticle of the invention. In FIG. 2, an aqueous solution containing gold salts is provided 20. The aqueous solution is mixed 24 with black tea, turmeric, curcumin (a component of turmeric) or cinnamon or a similar naturally occurring polyphenols- or flavanoids-rich plant material or specific reactive phytochemical components of such materials. Reactive phytochemcial components of tea include the catechins, theaflavins and thearubigins. Reactive components of cinnamon include linalool and catechin compounds.

The gold salts are reacted at room temperature 26 to form biocompatible gold nanoparticles that are stabilized with a coating of the polyphenols- or flavanoids-rich plant material. The entire process can be conducted at room temperature in a reasonable period of a time. The process can also be expedited by heating, such as by heating with microwaves.

Preferably, the black tea, turmeric, curcumin or cinnamon or similar naturally occurring polyphenols- or flavanoids-rich plant material is a powder. Stabilized, biocompatible gold nanoparticles are separated 28 from the reaction mixture by passing the reaction mixture through filter paper to remove the plant materials. The black tea, turmeric, curcumin or cinnamon or similar naturally occurring polyphenols- or flavanoids-rich plant material is preferably non-roasted. Powder or roots forms of turmeric can be used. Similarly, powder or bark chunk forms of cinnamon can be used.

Preferred gold salts used in methods of the invention are either sodium tetrachloraurate or aurochloric acid with naturally available black tea, turmeric, curcumin or cinnamon. in this embodiment, production of gold nanoparticles is achieved by simple mixing of black tea, turmeric, curcumin or cinnamon powder or leaves to an aqueous solution of aurochloric acid or sodium tetrachloroaurate. Gold nanoparticles produced by this process do not require any external chemical to stabilize the gold nanoparticles. While the invention is not limited to a particular mechanism and understanding of the reaction mechanism is not required to practice the described embodiments, it is believed that various phytochemicals present in tea, turmeric, cinnamon, and similar materials are responsible for providing a robust coating on gold nanoparticles and thus, rendering stability against agglomerations.

The method of FIG. 2 produces gold nanoparticles that require no further purification, that are biocompatible and stable. While the particles are stable as produced, an additional stabilizing agent such as gum Arabic can provide additional stability.

No further treatment is required prior to use of the stabilized, biocompatible gold nanoparticles produced by the method in biomedical applications. The method produces stabilized, biocompatible gold nanoparticles that are suitable for use within the body (in vivo) for diagnostic imaging using X-ray contrast CT imaging for the detection of various diseases, disorders and cancer. The gold nanoparticles are also suitable as X-ray enhancers in X-ray therapy of diseases including cancer. The stabilized, biocompatible gold nanoparticles are also useful for localized heating of targeted cells, namely hyperthermia treatment. Stabilized, biocompatible gold nanoparticles of the invention are suitable for direct administration into the human body through oral or intravenous routes.

Stabilized, biocompatible gold nanoparticles of the invention are biologically benign and therefore are also useful as coatings on skin, hair, for direct injections into specific tissue, for ingestion, etc. Stabilized, biocompatible gold nanoparticles are immediately suitable after fabrication by the FIG. 2 method for use in clinical CT imaging, X-ray induced cancer therapy and other diagnosis and therapeutic procedures, including cancer detection and treatment in animals and human beings. Stabilized, biocompatible gold nanoparticles of the invention are opaque to X-rays and provide excellent contrast between healthy and diseased tissue when viewed through X-ray CT images. They can be used in X-ray CT imaging for molecular imaging of cancer and various other diseases. They can also be used for the selective absorption of high energy X-rays in cancer therapy. Stabilized, biocompatible gold nanoparticle particles of the invention possess inherent high affinity toward gastrin releasing peptide receptors present on various types of cancerous cells such as cancerous cells of the prostate and breast cancer cells.

Experimental Results

Stabilized, biocompatible gold nanoparticles have been produced in experiments that are consistent with the FIG. 2 method of fabrication. The stabilized, biocompatible gold nanoparticles were tested and characterized. The experiments will now be described, and artisans will appreciate additional aspects of the invention from the experiments. Artisans will also recognize that the experiments do not limit the invention and that commercial scale fabrication processes consistent with the invention may use different equipment, batch sizes and specific procedures related to the equipment and batch sizes.

Figure 3:
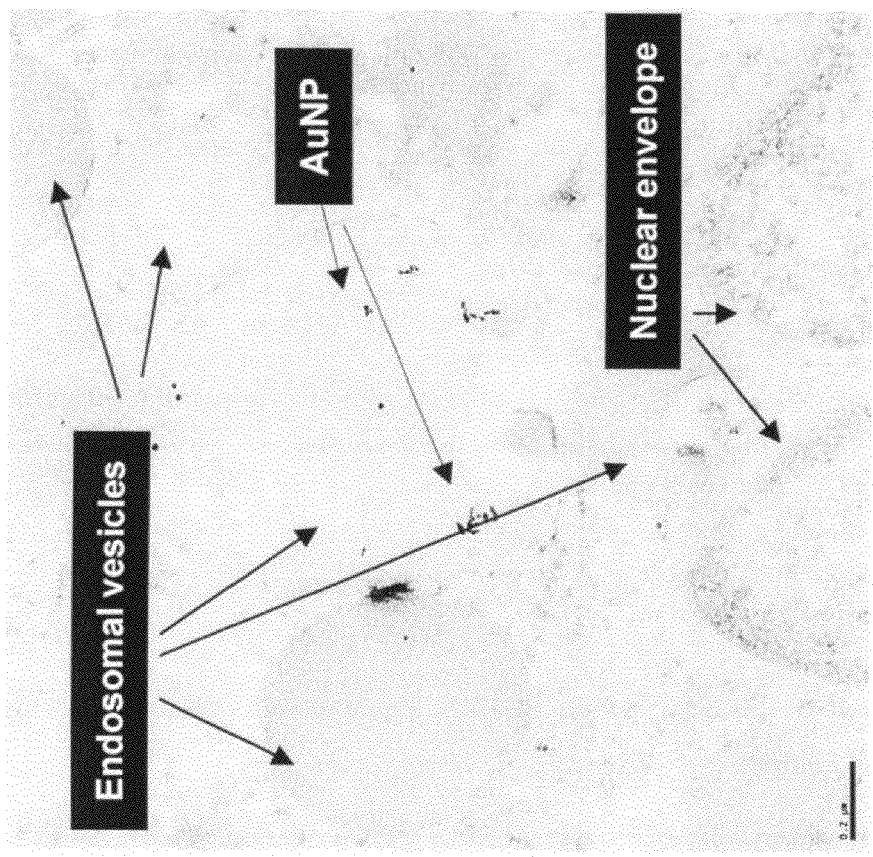
FIG. 3 is an image of a cell that has internalized stabilized, biocompatible gold nanoparticles of the invention.

On experiment was conducted to test stabilized, biocompatible gold nanoparticles of the invention for interaction with cancer cells. FIG. 3 shows an image taken of stabilized, biocompatible gold nanoparticles internalized in cancer cells. The internalization of nanoparticles may be mediated through endosomal uptake by cells.

Stabilized, biocompatible gold nanoparticles were produced in separate experiments using tea, turmeric and cinnamon. Details of the conditions used in the experiments are shown in Table 1.

TABLE 1

Gold Nanoparticle Production Processes (Examples provided here are for 1-2 Liter scale)

|  | Tea | Turmeric | Cinnamon |
| --- | --- | --- | --- |
| Solvent | Water | Water | Water |
| Process time | Less than 1 min | 2 minutes | 15 minutes |
| Reaction temperature | Room Temperature | Room Temperature | Room Temperature |
| Size | 5-10 nm | 7-12 nm | 10-15 nm |
| Stability | High | High | Moderate |
| Reproducibility | High | High | High |
| Biocompatibility | Suitable for in vivo | Suitable for in vivo | Suitable for in vivo |
| Eco friendly | Zero-chemicals used | Zero-Chemicals used | Zero-Chemicals used |
| Scalability | Up to 2 liter | Up to 1 liter | Up to 1 liter |

Sodium tetrachloroaurate and aurochloric acid used in the experiments were obtained from Aldrich Chemicals and used without further purification. Turmeric, Cinnamon and Black Tea were obtained from several geographic locations. Organic forms of these spices were obtained from authentic growers.

Synthesis Using Black Tea

Gold nanoparticles were prepared by suspending 12 omg of Black Tea in 6 ml of doubly ionized (DI) water. To this suspension 0.1 ml of 0.1M $NaAuCl_4$ solution was added. The color of the solution changes from light yellow to dark purple within 10-30 minutes indicating the formation of gold nanoparticles. The reaction is complete in 4-6 hours. The reaction can be expedited by heating. For example, the contents can be heated via in microwave heating for 5-10 seconds. The pH of the solution after reaction is 3-4 and can be adjusted to physiological pH by adding 0.1 ml of phosphate buffer concentrate (pH 7) to whole volume. The nanoparticles generated by using Tea were found to be stable for over a period of 4 weeks. Further stabilization of gold nanoparticles generated from Tea was achieved by adding 0.2 ml of gum Arabic solution.

Figure 4:
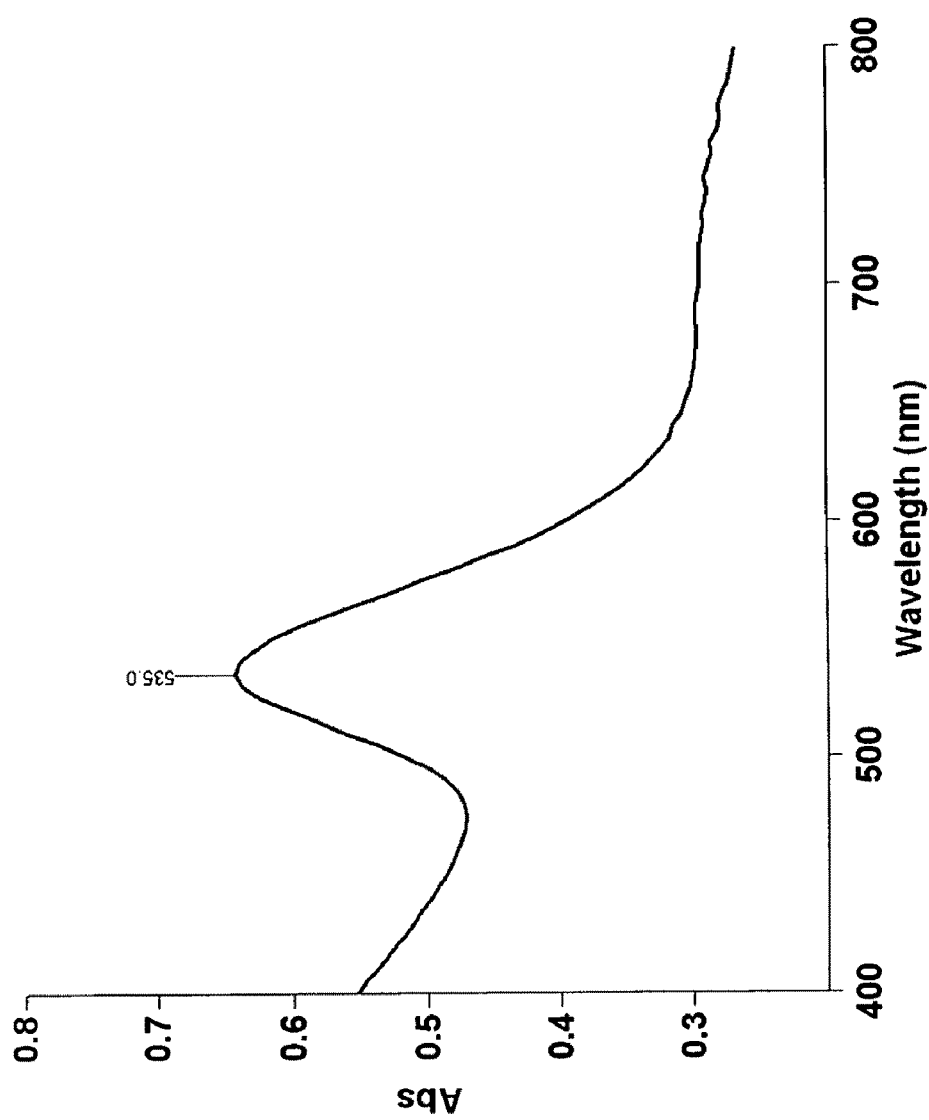
FIG. 4 is a measured UV-visible spectrum of stabilized, biocompatible gold nanoparticles of the invention produced in experiments with a coating generated by black tea.

The formation of stabilized, biocompatible gold nanoparticles using black tea was confirmed by taking the UV-visible spectrum of gold nanoparticles generated and stabilized by black tea, which is shown in FIG. 4. FIG. 4 shows the characteristic plasmon resonance band of gold nanoparticles in the ultra violet spectrum. Scanning electron micrographs also revealed the formation of stabilized, biocompatible gold nanoparticles.

In vitro stability studies were performed by challenging 0.5 ml of black tea stabilized gold nanoparticle solutions in aqueous media with 0.5 ml each of 0.2M Cysteine, 0.2M Histidine and 0.2M Human Serum Albumin (HSA) solutions. The stability and the identity of the black tea stabilized gold nanoparticles were measured by recording UV absorbance at 2 hrs through 7 days. The plasmon resonance band at 535 nm confirmed the retention of nanoparticulates in all the above mixtures. Additionally, in vitro stability measurements included challenging 0.5 ml of black tea stabilized gold nanoparticles in aqueous media with 0.5 ml of 35% saline. TEM measurements inferred the retention of the nanoparticulate composition in all the above in vitro studies Synthesis Using Turmeric Stabilized, biocompatible gold nanoparticles were also prepared by suspending 100 mg of turmeric in 6 ml of doubly ionized (DI) water. To this suspension 0.1 ml of 0.1M $NaAuCl_4$ solution was added. The color of the solution changes from light yellow to dark purple within 10-30 minutes indicating the formation of turmeric stabilized gold nanoparticles. The reaction is complete in 4-6 hours. The reaction can be expedited by heating. Heating can be conducted, for example, by heating the contents in microwave for 5-10 seconds. The pH of the turmeric stabilized gold nanoparticle solution is 3-4 and can be adjusted to physiological pH by adding 0.1 ml of phosphate buffer concentrate (pH 7) to whole volume. The nanoparticles generated using turmeric are stable for over a period of 4 weeks. Further stabilization of gold nanoparticles generated from turmeric was achieved by adding 0.2 ml of gum Arabic solution.

Figure 5:
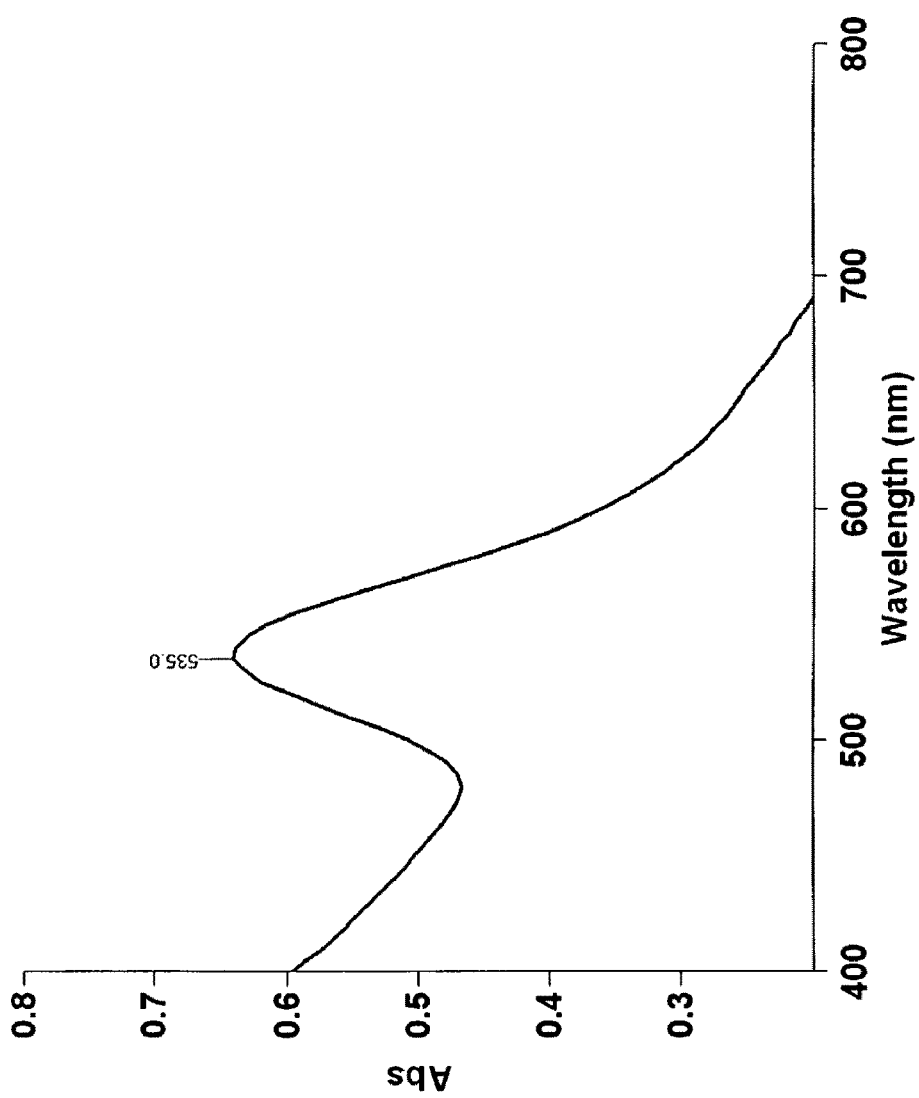
FIG. 5 is a measured UV-visible spectrum of stabilized, biocompatible gold nanoparticles of the invention produced in experiments with a coating generated by turmeric.

The formation of stabilized, biocompatible gold nanoparticles using turmeric was confirmed by taking the UV-visible spectrum of gold nanoparticles generated and stabilized by black tea, which is shown in FIG. 5. FIG. 5 shows the characteristic plasmon resonance band of gold nanoparticles in the ultra violet spectrum. Scanning electron micrographs also revealed the formation of stabilized, biocompatible gold nanoparticles.

In vitro stability studies were performed by challenging 0.5 ml of turmeric stabilized gold nanoparticle solutions in aqueous media with 0.5 ml each of 0.2M Cysteine, 0.2M Histidine and 0.2M Human Serum Albumin (HSA) solutions. The stability and the identity of turmeric stabilized gold nanoparticles were measured by recording UV absorbance at 2 hrs through 7 days. The plasmon resonance band at 535 nm confirmed the retention of nanoparticulates in all the above mixtures. Additionally, in vitro stability measurements included challenging 0.5 ml of turmeric stabilized gold nanoparticle solutions in aqueous media with 0.5 ml of 35% saline. TEM measurements inferred the retention of the nanoparticulate composition in all the above in vitro studies.

Synthesis Using Cinnamon

Stabilized, biocompatible gold nanoparticles were prepared by suspending 50 mg of Cinnamon in 6 ml of doubly ionized (DI) water. To this suspension 0.1 ml of 0.1M $NaAuCl_4$ solution was added. The color of the solution changes from light yellow to dark purple within 10-30 minutes indicating the formation of cinnamon stabilized gold nanoparticle. The reaction is complete in 4-6 hours. The reaction can be expedited by heating, such as by microwave heating. The pH of the cinnamon stabilized gold nanoparticle solution is 3-4 and can be adjusted to physiological pH by adding 0.1 ml of phosphate buffer. The cinnamon stabilized gold nanoparticles are stable for over a period of 4 weeks. Further stabilization can be achieved by adding 0.2 ml of gum Arabic solution.

Figure 6:
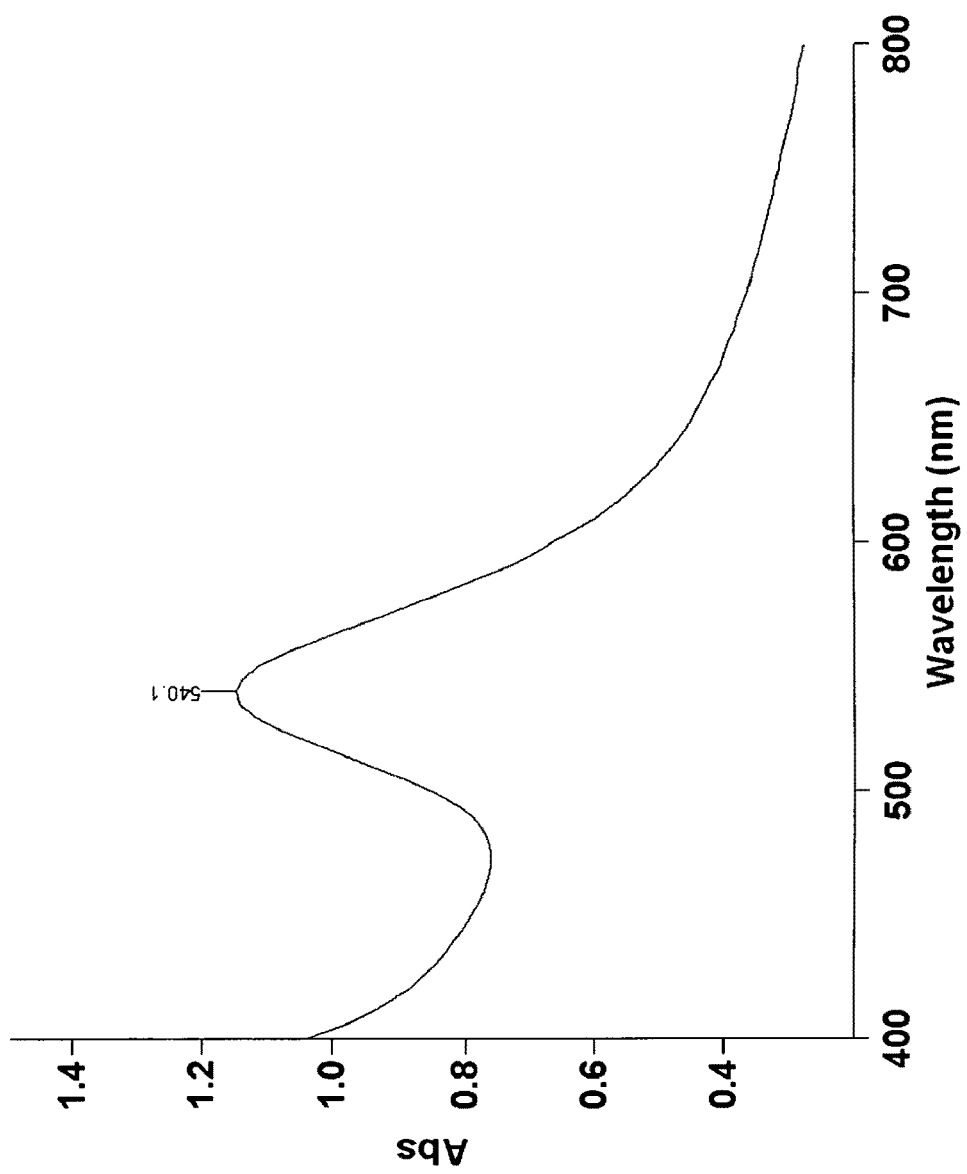
FIG. 6 is a measured UV-visible spectrum of stabilized, biocompatible gold nanoparticles of the invention produced in experiments with a coating generated by cinnamon.

The formation of stabilized, biocompatible gold nanoparticles using cinnamon was confirmed by taking the UV-visible spectrum of gold nanoparticles generated and stabilized by cinnamon, which is shown in FIG. 6. FIG. 6 shows the characteristic plasmon resonance band of gold nanoparticles in the ultra violet spectrum. Scanning electron micrographs also revealed the formation of stabilized, biocompatible gold nanoparticles.

In vitro stability studies were performed by challenging 0.5 ml of cinnamon stabilized gold nanoparticles in aqueous media with 0.5 ml each of 0.2M Cysteine, 0.2M Histidine and 0.2M Human Serum Albumin (HSA) solutions. The stability and the identity of cinnamon stabilized gold nanoparticles were measured by recording UV absorbance at 2 hrs through 7 days. The plasmon resonance band at 535 nm confirmed the retention of nanoparticulates in all the above mixtures. Additionally, in vitro stability measurements included challenging 0.5 ml of cinnamon stabilized gold nanoparticles in aqueous media with 0.5 ml of 35% saline. TEM measurements inferred the retention of the nanoparticulate composition in all the above in vitro studies.

Synthesis Using Tea and Various Conditions

Stabilized, biocompatible stabilized gold nanoparticles were prepared under various conditions using Tea. In the additional Tea experiments, the $NaAuCl_4$ gold salt was procured from Alfa-Aesar. Average size and size distribution of stabilized gold nanoparticles synthesized were determined by processing of TEM images. Asorption measurements were made using a Varian Cary 50 UV-Vis spectrophotometers with 1 mL of stabilized gold nanoparticle solution in disposable cuvvettes of 10 mm path length. The various particles in the additional experiments will be designated with numerical extensions, e.g., −1, −2, −3 . . . .

Tea Initiated and Stabilized Gold Nanoparticles (T-AuNP-1)

To a 10 mL vial was added 6 mL of doubly ionized water (DI), followed by the addition of 100 mg of Tea (Darjeeling Tea). The reaction mixture was stirred continuously at 25° C. for 15 min. To the stirring mixture was added 100 µL of 0.1 M $NaAuCl_4$ solution (in DI water). The color of the mixture turned purple-red from pale yellow within 5 minutes after the addition indicating the formation of stabilized gold nanoparticles. The reaction mixture was stirred for an additional 15 minutes. The stabilized gold nanoparticles thus formed were separated from residual tea leaves immediately using a 5 micron filter and were characterized by UV-Vis absorption spectroscopy and TEM analysis.

Tea Initiated and Gum Arabic Stabilized Gold Nanoparticles (T-AuNP-2)

To a 10 mL vial was added 0.012 g of Gum Arabic, 6 mL of doubly ionized water (DI), followed by the addition of 100 mg of Tea (Darjeeling Tea). The reaction mixture was stirred continuously at 25° C. for 15 min. To the stirring mixture was added 100 µL of 0.1 M $NaAuCl_4$ solution (in DI water). The color of the mixture turned purple-red from pale yellow within 10 minutes indicating the formation of stabilized gold nanoparticles. The reaction mixture was stirred for an additional 15 minutes. The stabilized gold nanoparticles thus formed were separated from residual tea leaves immediately using a 5 micron filter and were characterized by UV-Vis absorption spectroscopy and TEM.

Tea Initiated and Stabilized Gold Nanoparticles at 40° C. (T-AuNP-3)

To a 10 mL vial was added 6 mL of doubly ionized water (DI), followed by the addition of 100 mg of Tea (Darjeeling Tea). The reaction mixture was stirred continuously at elevated temperature (~40° C.) for 5 min. To the warm stirring mixture was added 100 µL of 0.1 M $NaAuCl_4$ solution (in DI water). The color of the mixture turned purple-red from pale yellow instantly indicating the formation of stabilized gold nanoparticles. The reaction mixture was stirred for an additional 5 minutes. The stabilized gold nanoparticles in DI water were separated from residual tea leaves immediately using a 5 micron filter and were characterized by UV-absorption spectroscopy and TEM analysis.

Tea Initiated and Gum Arabic Stabilized Gold Nanoparticles at 40° C. (T-AuNP-4)

To a 10 mL vial was added 0.012 g of gum Arabic, 6 mL of doubly ionized water (DI), followed by the addition of 100 mg of Tea (Darjeeling Tea). The reaction mixture was stirred continuously at elevated temperature (~40° C.) for 5 min. To the warm stirring mixture was added 100 µL of 0.1 M $NaAuCl_4$ solution (in DI water). The color of the mixture turned purple-red from pale yellow in about 5-10 min indicating the formation of stabilized gold nanoparticles. The reaction mixture was stirred for 5 more minutes. The stabilized gold nanoparticles in DI water were separated immediately using a 5 micron filter. The tea/gum Arabic stabilized gold nanoparticles (T-AuNP-4) were characterized by UV-absorption spectroscopy and TEM analysis.

Tea Extract (>80% Theaflavins) Initiated/Stabilized Gold Nanoparticles (Tea-AuNP-5)

To a 20 mL vial was added 0.035 g of Tea extract (>80% theaflavins; Sigma), 6 mL of doubly ionized water (DI). The reaction mixture was stirred continuously at 25° C. for 3 min. To the stirring mixture was added 100 µL of 0.1 M $NaAuCl_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~540 nm indicated the formation of stabilized gold nanoparticles. TEM measurements confirmed the size distribution of stabilized gold nanoparticles.

Epicatechin Gallate Initiated/Stabilized Gold Nanoparticles (Tea-AuNP-6)

To a 20 mL vial was added 2.2 mg of Epicatechin gallate, 6 mL of doubly ionized water (DI). The reaction mixture was stirred continuously at 25° C. for 3 min. To the stirring mixture was added 100 µL of 0.1 M $NaAuCl_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Catechin Initiated/Stabilized Gold Nanoparticles (Tea-AuNP-7)

To a 20 mL vial was added 2.2 mg of Catechin, 6 mL of doubly ionized water (DI). The reaction mixture was stirred continuously at 25° C. for 3 min. To the stirring mixture was added 100 µL of 0.1 M $NaAuCl_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Catechin Gallate Initiated/Stabilized Gold Nanoparticles (Tea-AuNP-8)

To a 20 mL vial was added 2.2 mg of Catechin gallate, 6 mL of doubly ionized water (DI). The reaction mixture was stirred continuously at 25° C. for 3 min. To the stirring mixture was added 100 µL of 0.1 M $NaAuCl_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Epicatechin Initiated/Stabilized Gold Nanoparticles (Tea-AuNP-9)

To a 20 mL vial was added 2.2 mg of Epicatechin, 6 mL of doubly ionized water (DI). The reaction mixture was stirred continuously at 25° C. for 3 min. To the stirring mixture was added 100 µL of 0.1 M $NaAuCl_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Epigallocatechin Initiated/Stabilized Gold Nanoparticles (Tea-AuNP-10)

To a 20 mL vial was added 2.2 mg of Epigallocatechin, 6 mL of doubly ionized water (DI). The reaction mixture was stirred continuously at 25° C. for 3 min. To the stirring mixture was added 100 µL of 0.1 M $NaAuCl_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Epigallocatechin Gallate (EGCG) Initiated/Stabilized Gold Nanoparticles (Tea-AuNP-11)

To a 20 mL vial was added 2.2 mg of Epigallocatechin gallate, 6 mL of doubly ionized water (DI). The reaction mixture was stirred continuously at 25° C. for 3 min. To the stirring mixture was added 100 µL of 0.1 M $NaAuCl_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

In Vitro Stability Studies of (T-AuNP-1-4) Stabilized Gold Nanoparticles

In vitro stabilities of the four different tea-mediated stabilized gold nanoparticles (T-AuNP, 1-4) were tested in the presence of NaCl, cysteine, histidine, HSA and BSA solutions. Typically, 1 mL of stabilized gold nanoparticle solution was added to glass vials containing 0.5 mL of 5% NaCl, 0.5% cysteine, 0.2 M histidine, 0.5% HSA, 0.5% BSA solutions respectively and incubated for 30 min. The stability and the identity of stabilized gold nanoparticles (T-AuNP 1-4) were measured by recording UV absorbance after 30 min. A plasmon resonance band at ~535 nm confirmed the retention of nanoparticulates in all the above mixtures. TEM measurements inferred the retention of the nanoparticulate compositions in all the above four different gold nanoconstructs signifying robust nature of these nanoparticles under in vitro conditions.

Cellular Internalization of T-AuNPs

Minimum essential medium (MEM with nonessential amino acids, powdered), HEPES, bovine insulin, streptomycin sulfate, penicillin-G, were obtained from Sigma Chemical Company (St. Louis, Mo.); all were cell culture tested when available. Bovine calf serum, phenol red (sodium salt), and lyophilized trypsin were obtained from Gibco BRL (Grand Island, N.Y.). MCF-7 breast cancer cells and PC-3 prostate cancer cells were obtained from V. Craig Jordan, University of Wisconsin-Madison and ATCC respectively. MCF-7 cells were maintained in MEM with nonessential amino acids, 10 pg/ml phenol red, 10 mM HEPES, 6 ng/ml insulin, 100 units/ ml penicillin, 100 pg/ml streptomycin, and 5% charcoal-stripped calf serum (maintenance medium). PC-3 cells were maintained in RPMI medium supplemented with 4.5 g/L D-glucose, 25 mM HEPES, 0.11 g/L sodium pyruvate, 1.5 g/L sodium bi carbonate, 2 mM L-glutamine and 10% FBS and antibiotics.

Cell Internalization Studies:

About 16,000 cells were plated into each well in a 6 well plate and this plate was incubated at 37° C. for 18.0-20.0 hrs to allow the cells to recover. After the cells were recovered the media from each well was aspirated and fresh growth media was added (about 4 mL per each well). Cells were allowed to grow for 3 days changing the media every alternate day. On the $5^{th}$ day, 25 micro molar concentrations of T-AuNPs solutions were added to each well. (Note: 25 µm stabilized gold nanoparticles solution is made up with the media itself). After adding the sample, plate was incubated for 4 h at 37° C. Media was aspirated from each well after 4 h and the cell layer was rinsed with CMFH-EDTA (Calcium-Magnesium-Free-Hark's+HEPES-EDTA) solution to remove all traces of serum which contains trypsin inhibitor. About 0.5 mL of Trypsin-EDTA solution was added to each well and cells were observed under an inverted microscope until cell layer is dispersed. 4.0 mL of complete growth medium was added to each well and cells were aspirated by gently pipetting. The cell suspension was transferred into to a centrifuge tube and centrifuged at approximately 125×g for 5 to 10 minutes. The cells were washed thoroughly with chilled PBS, pelleted by centrifugation and fixed with 0.1 M Na-Cacodylate buffer containing 2% glutaraldehyde and 2% paraformaldehyde. The pellets were post fixed with 1% osmium tetraoxide, dehydrated and embedded in Epon/Spurr's resin and 80 nm sections were collected and placed on TEM grids followed by sequential counter staining with urenyle acetate and lead citrate. TEM grids were observed under TEM (Joel 1400) and images were recorded at different magnifications.

Cytotoxicity Evaluations

MTT Cell Proliferation Assay kit was obtained from ATCC. For the cytotoxicity evaluation of these nanoparticles, MTT assay was done as described by supplier. Briefly, $1 \times 10^5$ cells/ml cells at the exponential growth phase were taken in a flat-bottomed 96-well polystyrene-coated plate and were incubated for 24 h in $CO_2$ incubator at 5% $CO_2$ and 37° C. Series of dilutions like 10, 25, 50, 100, and 150 µM of T-AuNP-1 were made in the medium. Each concentration was added to the plate in quadruplet manner. After 24 h of incubation, 10 µl/well MTT (stock solution 5 mg/ml PBS) was added for 6 h and formazan crystals so formed were dissolved in 100 µl detergent. The plates were read in a microplate reader (Dynastic MR 5000, USA) operating at 570 nm. Wells with complete medium, nanoparticles, and MTT, but without cells were used as blanks. All experiments were performed 3 times in quadruplets, and the average of all of the experiments has been shown as cell-viability percentage in comparison with the control experiment, while gold untreated controls were considered as 100% viable.

Characterization of the Tea Stabilized Gold Nanoparticles Under Various Conditions Absorption measurements indicated that the plasmon resonance wavelength, $\lambda_{max}$ of various T-AuNPs is ~535 nm. The sizes of T-AuNPs are in the range of 15-42 nm as measured from TEM techniques The phenolics and other phytochemicals within tea not only result in effective reduction of gold salts to their corresponding nanoparticles but their chemical framework wrap around the stabilized gold nanoparticles to provide excellent robustness against agglomeration.

Size and Morphology:

TEM measurements on T-AuNPs 1-4 show that particles are spherical in shape within the size range of 16-35 nm. Size distribution analysis of T-AuNPs confirm that particles are mono disperse. DCS technique measures size of the nanoparticle by determining the time required for nanoparticles to traverse a sucrose density gradient created in a disc centrifuge. Both the techniques, TEM and DCS, provide sizes of metallic-gold cores. Gold nanoparticulate sizes measured by TEM and DCS, were in good agreement and are in the range 16-35 nm. Dynamic light scattering was employed to calculate the size of gold coated with phytochemicals (hydrodynamic radius). The tea phytochemicals coatings on stabilized gold nanoparticles are expected to cause substantial changes in the hydrodynamic radius of T-AuNPs. Hydrodynamic diameter of T-AuNP-1 and T-AuNP-2 as determined from DLS measurements gave a values of 105±1 and 165±1 respectively, suggesting that tea phytochemicals (catechins, theaflavins and thearibigins) are capped on stabilized gold nanoparticles. The measurement of charge on nanoparticles, Zeta Potential ($\zeta$), provides crucial information on the stability of the nanoparticle dispersion. The magnitude of the measured zeta potential is an indication of the repulsive forces that are present and can be used to predict the long-term stability of the nanoparticulate dispersion. The stability of nanoparticulate dispersion depends upon the balance of the repulsive and attractive forces that exist between nanoparticles as they approach one another. If all the particles have a mutual repulsion then the dispersion will remain stable. However, little or no repulsion between particles, lead to aggregation. Negative zeta potential of −32±1 and −25±1 for T-AuNP-1 and T-AuNP-2 indicates that the particles repel each other and there is no tendency for the particles to aggregate.

Large Scale Synthesis Optimization

Synthetic conditions have been optimized for the quantitative large scale conversions of $NaAuCl_4$ to the corresponding AuNPs using tea leaves. The nature and chemical roles of different phytochemicals in tea leaves for the production of T-AuNPs are summarized in the following sections. The main phytochemicals present in black tea leaves consist of water soluble Catechins (Catechin, Epicatechin, Epicatechin gallate, Epigallocatechin, Epigallocatechin gallate etc.,), Theaflavins (Theaflavin, Theaflavin 3-gallate, Theaflavin 3'-gallate, Theaflavin 3,3'-gallate etc.,) and Thearubigins, which are oligomers of catechins of unknown structure. Generation of T-AuNPS using tea leaves involves aqueous media. Experiments have systematically investigated the roles of catechins and theaflavins for the generation and stabilization of AuNPs.

Role of Catechins

The series of independent experiments for the generation of stabilized gold nanoparticles using commercially available catechins (Catechin, Epicatechin, Epicatechin gallate, Catechin gallate, Epigallocatechin, Epigallocatechin gallate) provide the necessary information to confirm that catechins are excellent reducing and stabilizing agents to reduce Au(III) to stabilized gold nanoparticles. The reactions went to completion within 30 min. Absorption measurements indicated that the plasmon resonance wavelength, $\lambda_{max}$ T-AuNPs are ~530 nm. The size of the T-AuNPs is found to be 15-52 nm as measured from the TEM images. The gold nanoparticles obtained using catechin, and epigallocatechin gallate (EGCG) showed excellent stability which was conformed by their in vitro stability studies. The stabilized gold nanoparticles obtained using epigallocatechin and epicatechin showed minimum stability, thus generating the formation of brown suspensions. To further investigate the reduction potential of all the catechins, the formation of stabilized gold nanoparticles using gum Arabic (a glyco protein) as stabilizer was also tested. The experiments revealed that all the catechins (Catechin, Epicatechin, Epicatechin gallate, Epigallocatechin, Catechin gallate, Epigallocatechin gallate) act as excellent reducing agents to reduce the Au(III) to stabilized gold nanoparticles. The nanoparticles thus generated showed improved stability against various salts and serum proteins. The experiments unambiguously uncover that catechin and epigallocatechin gallate (EGCG) have excellent reducing and stabilizing capabilities to reduce and stabilize the stabilized gold nanoparticle.

(ii) Role of Tea Extract (>80% Theaflavins)

The role of theaflavins in the generation of stabilized gold nanoparticles was also investigated. The tea extract in these experiments was from Sigma-Aldrich and contained >80% theaflavins. Addition of aqueous solution of $NaAuCl_4$ to the theaflavin aqueous solution at 25° C. resulted in the formation of purple colored solutions within 30 minutes. The stabilized gold nanoparticles thus obtained by using theaflavin were characterized by UV-Vis absorption spectroscopy and TEM. Plasmon resonance band at ~535 nm indicated the formation of stabilized gold nanoparticles. TEM measurements confirmed the size distribution of stabilized gold nanoparticles. Detailed in vitro stabilities of the stabilized gold nanoparticles confirmed that the nanoparticles are extremely stable under various conditions. These results convincingly demonstrate the reducing and stabilizing capabilities of mixture of theaflavins. The determination of unambiguous roles of catechins and theaflavins will find applications in careful design of tumor specific imaging modalities.

The reservoir of non toxic phytochemicals in tea serves as a source of non toxic reducing agents with capabilities for in vivo administrations in situations that require generation of stabilized gold nanoparticles under in vivo conditions. The approach to gold nanoparticulate synthesis in the various tea experiments provides a universally applicable generalized synthetic route using phytochemicals available in tea and can provide for the fabrication of a library of stabilized gold nanoparticles with various non-toxic bioconjugates. One such example has been explored via the utilization of gum Arabic (GA), a commonly used non-toxic food additive. The example use of gum Arabic protein shows that bioconjugates can be used as a green platform to achieve excellent control over size and shape of nanoparticles.

The additional envirofriendly component, in the form of gum Arabic, also provides additional advantages. The use of gum Arabic along with Tea leaves resulted in an increase in the optical density (absorbance) in the UV-Vis spectra of reaction mixtures. This observation demonstrates that gum Arabic is likely serving as a biochemical platform to drive such reactions to completion with consequent production of well defined and uniform spherical stabilized gold nanoparticles. The effect of temperature on the formation of stabilized gold nanoparticles revealed that nanoparticle formation at elevated temperatures results in a randomly distributed spherical stabilized gold nanoparticles of sizes varying from 15-30 nm.

An issue of critical importance for in vivo imaging applications is the stability of AuNPs over a reasonable time period. The stability of T-AuNPs evaluated by monitoring the plasmon ($\lambda_{max}$) in 0.5% Cysteine, 0.2 M Histidine, 0.5% Human Serum Albumin (HSA), 0.5% Bovine Serum Albumin (BSA) or 5% NaCl solutions were evaluate over 30 min. The stability of T-AuNPs in pH 5, 7 and pH 9 phosphate buffer solutions was also tested. The plasmon wavelength in all the above formulations shifts ~1-5 nm, showing that the AuNPs are intact and that they demonstrate excellent in vitro stability in biological fluids at physiological pH For biomedical applications that require lower concentrations of AuNPs, it is vitally important that dilutions of AuNP solutions do not alter their characteristic chemical and photophysical properties. The effect of dilution on the stability of T-AuNPs under dilution was measured. Specifically, the plasmon resonance wavelength ($\lambda$max) was monitored after successive addition of 0.1 mL of doubly ionized (DI) water to 1 mL of AuNP solutions. The absorption intensity at $\lambda$max was found to be linearly dependent on the concentration of AuNPs, in accordance with Beer Lambert's law. The $\lambda$max of AuNPs did not change at very dilute conditions.

Cellular internalization studies was studied via incubation of aliquots of T-AuNPs with cancer cells. TEM images of prostate (PC-3) and breast tumor (MCF-7) cells post treated with T-AuNPs showed significant internalization of nanoparticles via endocytosis within the MCF-7 and PC-3 cells. The internalization of nanoparticles within cells could occur via processes including phagocytosis, fluid-phase endocytosis, and receptor-mediated endocytosis. The viability of both PC-3 and MCF-7 cells post internalization of T-AuNPs suggests that the phytochemical coating renders the nanoparticles to be non toxic to cells. Such internalization of stabilized gold nanoparticles, keeping the cellular machinery intact provides new opportunities for probing cellular processes via nanoparticulate-mediated imaging.

The cytotoxicity of T-AuNPs under in vitro conditions in Prostate (PC-3) and Breast (MCF-7) cancer cells were examined in terms of the effect of stabilized gold nanoparticles on cell proliferation by the MTT assay. Untreated cells as well as cells treated with 10, 25, 50, 100, and 150 µM concentrations of stabilized gold nanoparticles for 24 h were subjected to the MTT assay for cell-viability determination. In this assay, only cells that are viable after 24 h exposure to the sample are capable to metabolize a dye (3-(4,5-dimethylthiazol-2-yl)-2,5-diphenyltetrazolium bromide) efficiently and produce a purple coloured precipitate which is dissolved in a detergent and analyzed sphectrophotometrically. After 24 h of post treatment, PC-3, MCF-7 cells showed excellent viability even up to 150 µM concentrations of T-AuNP These results demonstrate that the phytochemicals within tea provide a non toxic coating on stabilized gold nanoparticles and corroborate the results as seen in the internalization studies discussed above. It is also important to recognize that a vast majority of Gold (I) and Gold (III) compounds exhibit varying degrees of cytotoxicity to a variety of cells. The lack of any noticeable toxicity of T-AuNPs provides new opportunities for the safe delivery and applications of such nanoparticles in molecular imaging and therapy.

Additional Characterization and Testing of Cinnamon Stabilized Gold Nanoparticles Fabricated at Various Conditions For additional characterization, of cinnamon stabilized gold nanoparticles, $NaAuCl_4$ was purchased from Alfa-Aesar. Trans-cinnamaldehyde, eugenol, cinnamyl acetate, cinnamyl alchohol, linalool, α-terpinene, (R)-(+)-Limonene, eugenyl acetate, linalyl acetate, catechin, epicatechin were purchased from Sigma (St. Louis, Mo.). All cell culture materials e.g. minimum essential medium (MEM with nonessential amino acids, powdered), HEPES, bovine insulin, streptomycin sulfate, penicillin-G, were obtained from Sigma (St. Louis, Mo.). Bovine calf serum, phenol red (sodium salt), and lyophilized trypsin were obtained from Gibco BRL (Grand Island, N.Y.).

Synthesis of Cinnamon Stabilized Gold Nanoparticles at Room Temperature (27-30° C.).

To a 20 mL vial was added 6 mL of doubly ionized (DI) water followed by the addition of 25 mg of cinnamon. The mixture was stirred continuously at 25° C. for 5 min. To the stirring mixture was added 100 μL of 0.1 M NaAuCl$_4$ solution (in DI water). The color of the mixture turned purple within 20 minutes after the addition of NaAuCl$_4$ indicating the formation of gold nanoparticles. The reaction mixture was stirred for an additional 10 minutes. The gold nanoparticle solution was separated from the residual cinnamon powder by means of a standard paper filter. The solution was further filtered through a 0.5 micron filter. Finally, the gold nanoparticles were characterized by UV-Vis absorption spectroscopy and TEM analysis.

Generation of Gold Nanoparticles by Individual Cinnamon Phytochemicals in Starch.

Attempted synthesis of gold nanoparticles from NaAuCl$_4$ was done with each of major components present in cinnamon as phytochemicals. Except linalool and catechin compounds, all other components have failed to produce nanoparticles by reducing NaAuCl$_4$. Starch, present as carbohydrate (80-90%) in cinnamon is used to stabilize the gold nanoparticles during the reduction process. The procedure of making gold nanoparticles by linalool and catechin compounds in starch is as follows: To a 20 mL vial was added 6 mL of doubly ionized (DI) water followed by the addition of 22.5 mg of starch. The mixture was stirred continuously at ~80° C. for 10 min. After dissolving the starch, the solution was cooled down to ~30° C. with continuous stirring at room temperature. To this solution was added 10 mg of linalool or 5 mg catechin or 5 mg epicatechin followed by 100 μL of 0.1 M NaAuCl$_4$ solution (in DI water). The color of the mixture turned purple-red within 30 minutes after the addition of NaAuCl$_4$ indicating the formation of gold nanoparticles. The solution was finally characterized by UV-Vis absorption spectroscopy and TEM analysis.

In Vitro Stability Studies of Cinnamon & Cinnamon Component Stabilized Gold Nanoparticles.

In vitro stability studies were performed by mixing gold nanoparticles to aqueous solutions of 10% NaCl, 0.5% cysteine, 0.2 M histidine, 0.5% HAS and 0.5% BSA. The stability of the conjugates was measured by monitoring the UV absorbance over the periods 30 min, 2 hrs and 7 days. A negligible change in plasmon band was observed in UV which confirmed the retention of nanoparticulate composition in all of the mixtures. TEM studies also inferred the stability of the nanoparticles in all of the in vitro studies.

Cell Culture of Cinnamon & Cinnamon Component Stabilized Gold Nanoparticles.

Human fibroblasts primary cultures were obtained from the Bond Life Science Centre at University of Missouri-Columbia. Fibroblast cells were maintained in DMEM with 10 pgmL$^{-1}$ phenol red, 10 mM HEPES, 100 units mL$^{-1}$ penicillin, 100 pgmL$^{-1}$ streptomycin, and 10% donor bovine serum (maintenance medium).

In Vitro Cytotoxicity measurements (MTT Assay) of Cinnamon & Cinnamon Component Stabilized Gold Nanoparticles.

The in vitro cytotoxicity evaluation of cinnamon stabilized gold nanoparticles was performed as described by the supplier (ATCC, USA). Briefly, 2×10$^4$ fibroblasts cells at the exponential growth phase were seeded in each well of a flat-bottomed 96-well polystyrene-coated plate and were incubated at 37° C. for 24 h in CO$_2$ incubator at 5% CO$_2$ environment. Series of dilutions like 25, 50, 125 and 165 μM (gold atoms) of these nanoparticles were made in the medium. Each concentration was added to the plate in pentaplet manner. After 24 h incubation, 10 μL per well MTT (stock solution 5 mgmL$^{-1}$ PBS) (ATCC, USA) was added for 24 h and formosan crystals so formed were dissolved in 100 μL detergent. The plates were kept for 18 h in dark at 25° C. to dissolve all the crystals and the intensity of developed color was measured by micro plate reader (Dynastic MR 5000, USA) operating at 570 nm wavelength. Wells with complete medium, nanoparticles, and MTT, but without cells were used as blanks. Untreated cells were considered 100% viable.

Cellular Uptake of Cinnamon & Cinnamon Component Stabilized Gold Nanoparticles.

MCF-7 breast cancer and PC-3 prostate cancer cells obtained from ATCC were used for the in-vitro cell internalization analyses. MCF-7 cells were maintained in MEM with nonessential amino acids, 10 pg/ml phenol red, 10 mM HEPES, 6 ng/ml insulin, 100 units/ml penicillin, 100 pg/ml streptomycin, and 10% FBS (maintenance medium). PC-3 cells were maintained in RPMI medium supplemented with 4.5 g/L D-glucose, 25 mM HEPES, 0.11 g/L sodium pyruvate, 1.5 g/L sodium bi carbonate, 2 mM L-glutamine and 10% FBS and antibiotics. Known concentration of cinnamon stabilized gold nanoparticles (100 μg/mL) were added to each type of cells (~10000 cells) and incubated for 4 h at 37° C. Following incubation, cells were washed three times with PBS, centrifuged into small pellets, and fixed with 2% glutaraldehyde 2% paraformaldehyde in sodium cacodylate buffer (0.1 M). The cells were further fixed with 1% buffered osmium tetraoxide and dehydrated in an ethanol series before embedding in Epon-Spurr epoxy resin. Sections (75-85 nm) were cut using Leica Ultracut UCT ultramicrotome and placed on a TEM grid. The sections were post-stained with uranyl acetate and lead citrate for organelle visualization. The prepared samples were viewed with JEOL 1400 Transmission Electron Microscope.

Biodistribution of Cinnamon & Cinnamon Component Stabilized Gold Nanoparticles in TRAMP Mice Model.

The biodistribution of Cin-AuNPs were assessed in two groups of TRAMP mice weighing ~20 g. The measurements were done by considering the amount of gold in various organs using AAS. For each time point, the animals were intravenously injected though tail with Cin-AuNP (200 μL, 3.75 mg/mL) and sacrificed after 4 h and 24 h time periods. The amount of gold in blood, brain, heart, kidney, muscle, pancreas, tumor, spleen, lung, liver and tail were determined to assess the tissue affinity for Cin-AuNPs. After 4 h of dosing, the average gold concentrations were negligible in blood, brain heart, kidney, muscle, pancreas and tumor while a very small amount of gold was observed in liver (65.0-77.0 μg/g of tissue) and tail (28.0-31.0 μg/g of tissue). The highest gold concentration was observed in lung (~482.0 μg/g of tissue). At 24 h after dosing, the gold concentrations remaining in the lung were not significantly different from those after 4 h, which suggests a good affinity of the AuNPs for lung tissues.

Sample Preparation for AAS.

Tissues were removed from −80° C. storage and allowed to partially thaw. Following partial thawing whole tissue samples were placed in a 15 ml clean graduated centrifuge tube with concentrated trace metal grade nitric acid (Fisher Scientific) and concentrated trace metal grade hydrochloric acid in 1:2 ratio and heated in an oven to 85° C. overnight (12-18 hr). The amount of acid depended on the weight of the tissue and the proportion used was 1 mg (tissue):1 μL (HNO$_3$):0.5 μL (HCl). After cooling, the digest was diluted in 1:10 ratio with ultra pure water for analysis. The mouse carcasses were homogenized by grinding into a fine powder using a stein mill and then ~1 g aliquots were digested and analyzed with the method described for the other mouse tissues.

AAS Analysis. All the samples were analyzed by furnace AAS using a standard curve spanning 0-100 micro grams/L. The furnace parameters were as specified in the user's manual for the Perkin-Elmer Analyst 800 ThGA graphite furnace. Quality-control materials (duplicates, spikes, and instrument-calibration verification) were within appropriate ranges.

CT Imaging

A Gammex/RMI Model 461 phantom was scanned using a Siemens volume zoom CT system. Five 5.0-mL glass vials containing aqueous solutions of various concentrations of Cin-AuNPs were placed in holders in the phantom. This arrangement presented a tissue like (solid water) background with Cin-AuNP contrast inclusions. Scans were performed at tube voltages of 80 and 140 kVp at the same level in the phantom. Images were reconstructed in 4-mm-thick slices with a field of view of 208 mm. Evaluation of the contrast enhancement contribution of Cin-AuNPs was carried out by loading the digital CT images in a standard display program and then selecting a region of interest on the resultant CT image for each sample and the background. Contrast enhancement was determined in $\Delta$HU for each mass concentration of Cin-AuNPs and each tube voltage.

Results Regarding Cinnamon & Cinnamon Component Stabilized Gold Nanoparticles.

The cinnamon stabilized gold nanoparticles (Cin-AuNP) were prepared by simple mixing of an aqueous solution of commercially available sodium tetrachloroaurate with cinnamon present in DI water. The reaction produced a purple-red color solution within 25 minutes at room temperature stirring. The absorbance profile revealed ad plasmon resonance wavelength $\lambda_{max}$ that appeared at ~540 nm. Other physicochemical properties, such as size, charge, and morphology of Cin-AuNPs were determined by transmission electron microscopy (TEM), differential centrifugal sedimentation (DCS, Disc Centrifuge, CPS Instruments), and dynamic light scattering (DLS). TEM and CPS were used to determine the core size of while DLS was used to evaluate the hydrodynamic size of phytochemicals coated gold nanoparticles. The TEM images showed the size and shape of the nanoparticles to be homogeneous with an average diameter of 13±5 nm and a narrow size distribution. As expected, the hydrodynamic size of cinnamon coated gold nanoparticles is greater than the core size measured by TEM and CPS. The negative zeta potential ($\zeta$) value (−31.0 mV) was determined for the Cin-AuNPs which provides the necessary repulsive forces for the particles to remain stable in solution.

The main phytochemicals present in cinnamon consist of essential oil (trans-cinnamaldehyde, eugenol, linalool, trans-cinnamic acid, terpenes and others; 1-4% by weight), polyphenols (catechin, epicatechin, anthocyanidin, catecin/epicatechin oligomers, kaempferitrin and others; 5-10% by weight) and carbohydrates (starch, polysaccharides, ash; 80-90% by weight). The phenolic compounds are known as potent antioxidants and thus, may play a major role in the overall reduction of $NaAuCl_4$. The systematically investigation revealed the roles of these phytochemicals for the generation and stabilization of AuNPs by interactions with $NaAuCl_4$ in aqueous media. Experiments with individual components did not result in gold nanoparticles production except linalool and catechin compounds. Both linalool and catechin compounds are therefore able to reduce $NaAuCl_4$ in aqueous media to produce purple-red solution of AuNPs. The chemical constitution of linalool and catechin compounds, used in generating the AuNPs comprises alcoholic —OH functional group which might be responsible for the reduction of the $NaAuCl_4$. The stabilization property for AuNPs was provided only by catechin. The antioxidant catechin uniquely showed both reducing and stabilization properties simultaneously during the nanoparticle formation.

The production of gold nanoparticles did not happen in the presence of any carbohydrates present in cinnamon at room temperature (~27-30° C.). Although the formation of AuNPs was observed with glucose, arabinose, galactose, rhammose at elevated temperatures (~80° C.), the stability was not sufficient to hold the nanoparticles in solution for significant length of time. However, when this reaction was carried out with initially dissolved starch or combination of individual carbohydrates, a similar purple-red color nanoparticle solution was obtained at room temperature with considerable stability to the AuNPs. These results unequivocally prove that while cinnamon phytochemicals are directly involved in $NaAuCl_4$ reduction, the present carbohydrates in cinnamon provide synergistic benefits to the overall reduction as well as stabilization processes.

Biomedical imaging application requires the stability of Cin-AuNP over a reasonable length of time. For this purpose, the challenging tests were performed in presence of 10% NaCl, cysteine, histidine, HSA and BSA solutions to determine the in vitro stabilities of the nano constructs in biological environments. The stability and the identity of Cin-AuNPs were measured by recording UV absorbance after 30 min. The plasmon resonance band at ~535 nm confirmed the retention of nanoparticulates in all the above mixtures. This indicates that the AuNPs are intact and thus, demonstrate excellent in vitro stability in biological fluids at physiological pH. TEM measurements also inferred the retention of the nanoparticulate compositions in all of the above different medium signifying robust nature of these nanoparticles under in vitro conditions. The stability also remain unaffected from pH 4 to 9 range, which implies that this Cin-AuNPs can be used in a wide pH range for various biomedical applications.

In vivo stability was also tested. The cytotoxicity of Cin-AuNPs was studied on primary human fibroblast cells under in vitro conditions by using a colorimetric cell-viability (MTT) assay. In the MTT assay, the cell viability was examined in terms of the absorbance of formazan (produced by the cleavage of MTT by dehydrogenases in living cells) at 570 nm which is directly proportional to the number of live cells. The experiment was performed using a wide range of concentrations of Cin-AuNPs (0, 25, 50, 125 and 165 µM (gold atoms)). The relative cell viability was ~90% for both 24 post treatment, not significantly different from the control. It has been reported that, a number of $Au^I$ and $Au^{III}$ complexes produces significant toxicity in cell culture media. In contrast, cinnamon phytocemicals coated gold nanoparticles does not show any toxicity in primary human fibroblast cultures. This observation ensures that the phytochemicals present in cinnamon effectively reduce $NaAu^{III}Cl_4$ in aqueous medium and provides the nontoxic surface coating for in vivo administrations in solutions.

Gold nanoparticles were also tested for their potential applications in drug delivery and intracellular imaging applications. The internalization of cinnamon phytochemicals coated gold nanoparticles in primary human fibroblast cells as well as in MCF-7 cancer cells was tested. After careful mixing of Cin-AuNPs to both cells, the gold nanoparticles incubated cells were washed vigorously using trypsin-EDTA solution followed by PBS (pH 7.4) to remove unbound gold nanorods. TEM images of Cin-AuNPs after entering into the cells showed that cinnamon phytochemicals coated gold nanoparticles are preferentially taken by both cells, cancerous as well as non-cancerous and appeared as an individual probes in the endosomes. This endosomal localization within the cells also ensures that the specific uptake of the gold is due to the receptor mediated endocytosis. Some of the nanoparticles also appeared as a large cluster outside the cell surface. The unique behaviour of Cin-AuNPs may provide new opportunities for understanding the cellular activities via nanoparticulate-mediated imaging.

The in vivo biodistribution studies following intravenous injection of the nanoparticles (3.75 mg/mL) were carried out in two groups of mice, each weighing ~20 g. Following 200 µL intravenous administrations of Cin-AuNPs, the mice were humanely sacrificed at 4 h and 24 h time periods. The collected blood and tissues (brain, heart, kidney, muscle, pancreas, tumor, spleen, lung, liver, tail, and muscle) were weighed and then frozen at −80° C. until sub sampling for analysis. Following partial thawing, whole tissues were digested with a mixture of concentrate $HNO_3$ and HCl acids (2:1) at 85° C. for overnight and the aliquots (diluted in water) were used for the analysis by AAS. The results of biodistribution studies for the intravenous route of administration of AuNPs, as estimated by AAS showed minimum uptake of AuNPs in nontarget organs. Limited binding with blood-plasma proteins also signifies the high in vivo stability, presumably due to the effective coating of the phytochemicals around the AuNPs. The significant accumulation of Cin-AuNPs in lung is almost identical from 4 h to 24 h. In addition, there is also a gradual accumulation of gold nanoparticles in liver for up to 24 h. This accumulation in the liver may be due to the uptake of nanoparticles by the macrophages (Kupffer cells) present in the liver. However, no toxic side effects were noted even at the 24-h post-injection period. Indeed, the excellent tolerance of high concentrations of injectable gold agents, for example, myochrysine as demonstrated in humans, provides significant future prospects in the application of AuNPs to tumor imaging and therapy.

The portions of IV dose retained in liver at 4 h and 24 h sacrifice time are ~9% and ~14%, while in lungs, ~17% and ~16% respectively for mice treated with Cin-AuNPs at doses of 200 µL solution (3.75 mg/mL). The amount of nanoparticulate gold found in the kidneys represented <1% of the total dose, thus indicating clearance of AuNPs at a slow pace. This shows that the gold nanoparticles of the invention are bound tightly within the cinnamon phytochemicals and that the carbohydrate part of the cinnamon apparently serves as a vehicle to deliver AuNPs to lungs and liver with minimal distribution of AuNPs to other nontarget organs. This selective delivery of Cin-AuNPs to lungs and liver may provides an unprecedented approach for the molecular imaging of target organs via X-ray contrast CT imaging.

CT imaging was carried out using phantoms prepared from Cin-AuNPs constructs as tissue mimics. Phantom images obtained at 80 and 140 kVp showed higher mean density of gold compared to the background results in a contrast differential ΔHU (HU=Hounsfield units). HU values were measured for increasing amounts of Cin-AuNPs and results showed a linear relationship observed between Cin-AuNPs concentration and ΔHU. Quantitative analysis of CT values for each concentration reveals that the cinnamon phytochemicals coated AuNPs has consistent attenuation coefficients with increasing concentrations. This result clearly suggests that Cin-AuNPs may have a high potential for use in in vivo CT imaging.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An environmentally friendly method for making biocompatible stabilized gold nanoparticles, the method comprising:
   mixing a polyphenols- or flavanoids-rich plant material reducing agent into an aqueous solution containing gold salts;
   permitting reaction of the gold salts, in the presence of said plant material and in the absence of any other reducing agent, to form stabilized, biocompatible gold nanoparticles.

2. The method of claim 1, wherein the plant material comprises black tea.

3. The method of claim 1, wherein the plant material comprises turmeric or its component curcumin.

4. The method of claim 1, wherein the plant material comprises cinnamon.

5. The method of claim 1, wherein the plant material comprises a powder.

6. The method of claim 1, wherein the plant material comprises bark or root material.

7. The method of claim 1, further comprising a step of heating the aqueous solution during said step of permitting reaction.

8. The method of claim 7, wherein said step of heating comprises microwave heating.

9. The method of claim 1, further comprising a step of adjusting the pH of the aqueous solution after said step of permitting reaction.

10. The method of claim 1 further comprising a step of adding a stabilizing agent to the aqueous solution after said step of permitting reaction.

11. The method of claim 10, wherein said stabilizing agent comprises gum Arabic.

12. The method of claim 1, wherein the gold salts comprises either sodium tetrachloraurate or aurochloric acid.

13. An environmentally friendly method for making biocompatible stabilized gold nanoparticles, the method comprising:
   mixing a reactive phytochemical component of polyphenols- or flavanoids-rich plant material reducing agent into an aqueous solution containing gold salts;
   permitting reaction of the gold salts to form stabilized, biocompatible gold nanoparticles in the presence of said plant material and no other reducing agent.

14. The method of claim 13, wherein the reactive phytochemical component comprises a catechin compound component of cinnamon.

15. The method of claim 13, wherein the reactive phytochemical component comprises a linalool compound component of cinnamon.

16. The method of claim 13, wherein the reactive phytochemical component comprises a catechin compound component of tea.

17. The method of claim 13, wherein the reactive phytochemical component comprises a theaflavin compound component of tea.

18. The method of claim 13, wherein the reactive phytochemical component comprises a thearubigins compound component of tea.

* * * * *

UNITED STATES PATENT AND TRADEMARK OFFICE
CERTIFICATE OF CORRECTION

PATENT NO.       : 8,333,994 B2
APPLICATION NO.  : 12/283935
DATED            : December 18, 2012
INVENTOR(S)      : Katti et al.

It is certified that error appears in the above-identified patent and that said Letters Patent is hereby corrected as shown below:

On the Title Page:

Item [56] Other Publications:
Left column, line 48      Please delete "94-44" and insert --94-99-- therefor.

In the Specification:

| | |
|---|---|
| Col. 2, line 24 | Please delete "nanoparticle" and insert --nanoparticles-- therefor. |
| Col. 4, line 30 | Please delete "phytochemcial" and insert --phytochemical-- therefor. |
| Col. 4, line 52 | After "cinnamon." please delete "in" and insert --In-- therefor. |
| Col. 5, line 48 | Please delete "On" and insert --One-- therefor. |
| Col. 6, line 22 | Please delete "omg" and insert --mg-- therefor. |
| Col. 6, line 56 | After "studies" please insert a --.--. |
| Col. 8, line 3 | Please delete "Asorption" and insert --Absorption-- therefor. |
| Col. 13, line 65 | Please delete "evaluate" and insert --evaluated-- therefor. |
| Col. 16, line 42 | Please delete "though tail" and insert --through the tail-- therefor. |
| Col. 16, line 48 | Please delete "brain heart" and insert --brain, heart-- therefor. |
| Col. 17, line 59 | Please delete "systematically" and insert --systematic-- therefor. |
| Col. 18, line 48 | Please delete "both 24 post" and insert --both 24h post-- therefor. |
| Col. 19, line 48 | Please delete "provides" and insert --provide-- therefor. |

Signed and Sealed this
Twenty-third Day of July, 2013

Teresa Stanek Rea
*Acting Director of the United States Patent and Trademark Office*